United States Patent [19]

Nakai et al.

[11] 4,036,990
[45] July 19, 1977

[54] METHOD OF INCREASING THE RATE OF SOLUBILITY OF MATERIALS OF LOW SOLUBILITY

[75] Inventors: Yoshinobu Nakai, Tokyo; Shin'Ichiro Nakajima, Napashino; Kiyoshi Sugiyama, Chiba, all of Japan

[73] Assignee: FMC Corporation, Philadelphia, Pa.

[21] Appl. No.: 557,723

[22] Filed: Mar. 12, 1975

[30] Foreign Application Priority Data

Sept. 13, 1974  Japan ............................... 49-104898

[51] Int. Cl.² ............................................. A01N 5/00
[52] U.S. Cl. .................................................. 424/361
[58] Field of Search ....................................... 424/361

[56] References Cited

PUBLICATIONS

Martin and Cook, "Remington's, Practice of Pharmacy" Comminution, Chapter 13, pp. 158–174, 1961.

*Primary Examiner*—Lewis Gotts
*Assistant Examiner*—Cary Owens
*Attorney, Agent, or Firm*—Charles H. Johnson

[57] ABSTRACT

The rate of solubility of a material of low solubility is increased by mixing the material with beta-1, 4-glucan and pulverizing the mixture. This simultaneously pulverizing both ingredients is found to produce a substantially different effect than when the ingredients are separately pulverized and then mixed together.

5 Claims, No Drawings

METHOD OF INCREASING THE RATE OF SOLUBILITY OF MATERIALS OF LOW SOLUBILITY

This invention relates to a method for pharmaceutical manufacture whereby the rate of release of active ingredients of low solubility is improved by use of beta-1, 4-glucan. More particularly, this invention relates to a method for pharmaceutical manufacture which comprises pulverizing the mixture of beta-1, 4-glucan and one or more active ingredients of low solubility for thereby improving the rate of release of solid internal medicines such as powder, granules, tablets, and capsules.

Controlling the time from the oral administration of a drug to a living body until it takes effect is the most important control of pharmacological reaction of drugs, and it is generally classified into two categories, an immediate release medicine and a sustained release medicine, by the length of time that an active ingredient takes effect.

For the purposes of manifesting effects quickly by curtailing the time of release of the ingredient immediate effects are, so far now, given by the injection but not yet sufficient with solid internal medicines where sooner release is desired in such cases as antibiotics which are applied to shock treatments by rapidly raising effective active ingredient's concentration in blood and an anodyne which requires rapid release.

In the past, in order to make ingredients of low solubility effective immediately, instead of making injection, they are changed into a form of water-soluble salts or minimize particle size by pulverizing, but it is not sufficient as it involves some defects and problems as stated below. Namely, when the active ingredient which can scarcely be released in the digestive tract is converted into a form of water-soluble salts which are easily dissolved in water, it is most liable to accompany changes of medical effects, and also it is not always possible to convert medicines of ingredients of low solubility into water-soluble salts of less side-effects and higher medical effects or into another form of derivatives. It is therefore inevitable at present to adopt other measures.

It is believed that minimization of the particle size of an active ingredient can certainly improve the rate of adoption as well as that of dissolution of the ingredient, but even so, the results are unsatisfactory in many cases which involve many defects in view of pharmaceutical engineering. In other words, when a single-ingredient medicine is pulverized mechanically, such grinding does not work efficiently so that it requires several hours and deteriorates a certain medicine by heat generation.

However, this invention has made possible to produce drugs with rapid release giving a long higher rate of solution to sparingly soluble drugs, which has been long a dream of the pharmaceutical engineering concerned.

The following is an outline of the experimental fact which led to this invention.

Beta-1, 4-glucan was pulverized in advance in a vibration mill and was mixed with phenacetin, which is a low solubility material, and the resultant mixture was pulverized in the vibration mill. A releasing test of the pulverized specimen was conducted by use of water as solvent, varying the mixing ratio of beta-1, 4-glucan to phenacetin in a range from 5 to 50% (w/w). Another release test was made with a mixture of solely pulverized phenacetin and beta-1, 4-glucan pulverized in advance to see the difference, these two tests showed that while solely pulverized phenacetin was released only by 20% in 10 minutes and 50% in 60 minutes, the co-pulverized mixture specimen of phenacetin and beta-1, 4-glucan resulted the release of phenacetin by 40% in 10 minutes and 70% in 60 minutes. When the concentration of phenacetin increases over 25%, there is a tendency that the rate of release is slightly lowered accordingly.

Further, the following experimental fact was ascertained. As to the method of mixing and simultaneous pulverizing phenacetin and beta-1, 4-glucan, it did not make any difference in improving the releasing time, either by simultaneously pulverizing phenacetin added to unpulverized beta-1, 4-glucan, or by pulverizing beta-1, 4-glucan for a certain period of time prior to pulverization of the mixture until the X-ray diffraction diagram thereof ceased to show a peak which is peculiar to beta-1, 4-glucan. The time required for simultaneous pulverization varies according to types of pulverizers, amount of specimens, pulverizing forces and other factors, but it is sufficient if it is done for several hours until the diffraction peak which is peculiar to crystalline substances ceases to exist in determination of X-ray diffraction, by the ordinary reflection or penetration methods. If the time is excessively extended, it loses energy efficiency and threatens to deteriorate the active ingredient. On the other hand, before the specimen becomes amorphous, namely, in such a state that X-ray diffraction peak is still observed, by ceasing simultaneous pulverization, the effect on improving the release time was lessened according to shortened pulverization time.

Almost no difference were shown in the releasing rate by content of phenacetin up to 5-25% (w/w) in pulverized mixtures, which obviously indicated a high releasing rate as compared with simply pulverized phenacetin, but when the content of phenacetin exceeded 25% (w/w), the effects of simultaneous pulverization with beta-1.4 glucan were gradually descending. As it is evident from this result, in the case that the objective of simultaneous pulverization with beta-1.4 glucan is phenacetin, while the less added amount of phenacetin to beta-1.4 glucan, the higher releasing ratio shown as compared with the control, the simply mixed groups, it is indicated that the simultaneously pulverized groups give a higher releasing effect in such an extensive range as 1:0.05-1:10 of ratios between beta-1.4 glucan and phenacetin. The above observation indicates that: such simultaneous pulverization accelerates releasing effect when less amount of phenacetin is added, and that when added amount of phenacetin is increased, the releasing rate is liable to be slightly lowered, and yet great is the releasing rate as compared with the control group, the simply mixed one. Consequently, when the releasing rate is accelerated by simultaneous pulverization with beta-1.4 glucan, the mixing ratio of beta-1.4 glucan to other active ingredients to be pulverized together is not to be limited. In short, the mixing rate could be determined according to the extent to which an acceleration effect on releasing rate is expected.

On the other hand, it was found that any pulverizer having a performance to make fine particles by mechanical grinding or crushing force such as a rotary ball mill, a vibration ball mill, a shaker mill and a hammer mill can be applied. The difference of releasing rate according to the variation of mixing ratio of beta-1, 4-glucan to phenacetin was as follows.

For 100 parts of beta-1, 4-glucan, phenacetin to be added thereto was prepared to be 5, 10, 25, 100, 500 and 1,000 parts in mixing and pulverizing together, the results are shown in Table 1.

neous pulverization with beta-1,4 glucan rather than by its single pulverization of it to produce its fine particles are: antifebrile alayestic drugs, drugs for neurolic disorders, sedative narcotic drugs, muscular relaxants, blood pressure depressors and anti-histamine drugs such as caffeine, camphor, quinine, dimethyl caprol, sulfamin, theophylline, theobromine, riboflavin, mephenesin, Table 1.

| Releasing time (min.) | Change of releasing rate of various mixtures by percentage ||||||||||||
|---|---|---|---|---|---|---|---|---|---|---|---|---|
| | (BG) 100 parts (ph) 5 parts || (BG) 100 parts (ph) 10 parts || (BG) 100 parts (ph) 25 parts || (BG) 100 parts (ph) 100 parts || (BG) 100 parts (ph) 500 parts || (BG) 100 parts (ph) 1000 parts ||
| | pulverized mixture | simply mixed | pulverized mixture | simply mixed | pulverized mixture | simply mixed | pulverized mixture | simply mixed | pulverized mixture | simply mixed | pulverized mixture | simply mixed |
| 10 | 42% | 20% | 41% | 20% | 40% | 20% | 38% | 20% | 35% | 20% | 34% | 20% |
| 60 | 72% | 50 | 71 | 50 | 70 | 50 | 65 | 50 | 65 | 50 | 62 | 50 |

(NOTE 1) Releasing solvent: Water
(NOTE 2) (BG) = beta-1, 4-glucan (ph) = phenacetin The reason for such acceleration of releasing rate by simultaneous pulverization is assumed as follows. In the case of usual crystalline ingredients, mechanical pulverizing force causes particles to fine at early stage of pulverization, but by further pulverization, it brings about so-called mechano-chemically balanced state, balancing aggregating force among particles with pulverizing force by external physical impact, which prevents further pulverization. Whereas, simultaneous pulverization with beta-1.4 glucan does supposedly develop releasing effect, cutting off aggregating force among particles of ingredients because of the existence of beta-1,4-glucan, which results in accelerating pulverization and noncrystallization of mixed groups without causing mechano-chemical balancing state.

In conducting a releasing test of a mixture of simultaneously pulverized samples of two or more, the effects found in this invention are well attained. For example, when simultaneously pulverized beta-1.4 glucan containing 10% of phenacetin and simultaneously pulverized beta-1.4 glucan containing 5% of caffeine were mixed at a rate of 50:50 to observe the releasing rate, it was found that each ingredient released at 41% and 50% after 10 minutes and 71% and 80% after 60 minutes respectively. The results of the releasing rate on the samples such as pulverized beta-1.4 glucan with phenacetin and beta-1.4 glucan with caffeine separately — 41% after 10 minutes, 71% after 60 minutes of phenacetin group, and 50% after 10 minutes and 80% after 60 minutes of caffeine group — exactly agreed with the above figures. Also, exactly the same result was obtained from another test pulverizing aminopyrin with beta-1,4 glucan and adding the aforementioned two mixtures. These results can surely be applied in the pharmaceutical field which deals with many kinds of active ingredients.

Incidentally, physical abrasion force caused by continuing pulverization raises the temperature of pulverized specimens, sometimes up to 60–70° C. Therefore, if the melting point of an active ingredient is lower than 70° C, simultaneous pulverization might not take effect, but it is possible to attain the object by cooling off the pulverizing operation. In comparison with pulverization of a single ingredient, simultaneous pulverization with beta-1,4 glucan is of advantage in preventing deterioration of active ingredients due to its minimum heat generation at mechanical pulverization.

The effects of the present invention as aforementioned were observed in the tests with other active ingredients of various kinds of low solubility. Active ingredients which indicate a rapid release by simultaneous pulverization with beta-1,4 glucan rather than by its single pulverization of it to produce its fine particles are: antifebrile alayestic drugs, drugs for neurolic disorders, sedative narcotic drugs, muscular relaxants, blood pressure depressors and anti-histamine drugs such as caffeine, camphor, quinine, dimethyl caprol, sulfamin, theophylline, theobromine, riboflavin, mephenesin, phenobarbital, thioacetazone, quercetin, rutin, salicilic acid, sodium theophyline, pyrobital, irgapyrine, digitoxin and glyceofluvin, as well as antibiotics such as acetylspiramycin, ampicillin, erythromycin, xathamycin, chloramphenicol, triacetyloleandomycin, nystatin, and various hardly soluble salts of these antibiotics.

Also, it takes effect in accelerating the release rate of steroid hormone type medicines such as methyltesterone methanthrosterone diol, progesterone, estrandiol benzoate, ethynylestradiol, desoxyeorticosterone acetate, cortisone acetate, hydrocortisone, hydrocortisone acetate and prednisolon, as well as nonsteroidic ovarian hormon type medicines such as dienesterol, hexastarol, diethylstylbene sterol dipropionate and chlorotrianisene.

Aforementioned simultaneously pulverized products of beta-1,4 glucan and active ingredients are applicable by usual means of preparation of powders, capsules, and tablets, when an excipient, a glidant, a disintegrating agent, a binder or other ingredients are mixed with them at a proper amount as necessary.

As described in the example 5, the tablets produced from wet granulation of mixed and simultaneously pulverized samples compressed by ordinary rotary tableting machine brought about a better release rate as compared with a medicine prepared by a simple pulverization of the component drugs.

The term "beta-1,4 glucan" referred to in the present invention means a product manufactured from a raw material which is a vegetable — active ingredient containing cellulose by means of chemical decomposition, mechanical grinding, ultrasonic waves or irradiation of high-energy beams such as gamma rays. Chemical decomposition may be carried out by any of the known methods. The mechanical grinding may be accomplished, either in a dry or wet process, using a ball mill, a hammer mill, a tube mill, or a vibrating mill, or by other crushing or attriting machine. The size reduction of the cellulosic substance by means of ultrasonic waves or by irradiation of high-energy electron beams may be effected by the method suggested by F. M. Morehead (Textile Research Journal, August, pp 549–553 (1950)) or by the method introduced by Imamura, Murakami et al. (Journal of Textile Science Society, Tokyo, Vol. 15 No. 11 (1959). These methods, however, are not always the only ones that are available for the purpose.

EXAMPLE 1

With 100 mg of chloramphenicol (listed in the Japanese pharmacopeia), 900 mg of beta-1,4 glucan was sealed in a stainless steel shaker mill and pulverized. The shaker mill had an inner volume of 38 cc and contained 17 balls diameter of which was 11 mm each. Pulverization was effected for 6 hours, taking account of the results of a preliminary test which was performed until crystalline peaks of both chloramphenicol and beta-1,4 glucan ceased to exist in the X-ray diffraction diagram. The following is an example of determination conditions of X-ray diffraction.

| Target | Cu | Filter | Ni |
|---|---|---|---|
| Voltage | 30 KV | Current | 10 mA |
| Count Range | 250 cps | Time Constant | 2 sec. |
| Scanning Speed | 20°/min. | Chart Speed | 40 m/m |

For the determination of the release rate of the active ingredient from the medicine prepared by mixing and simultaneous pulverization, 1 g of the powdered test specimen was placed in a beaker having an inner volume of 300 cc and a solvent was poured thereon. A stirrer was inserted in the contents of the beaker and rotated at a fixed rate. At fixed intervals, the contents were sampled and each specimen thus taken was passed through a glass filter to remove comminuted beta-1,4 glucan and obtain a liquid in which the active ingredients released from the mixed preparation were contained.

By using a double-beam U.V. spectrophotometer, the specimen was tested for chloramphenicol absorption spectra at $\lambda = 278$ mu, with its concentration calculated by means of the calibration curve method.

The determination was carried out in a constant temperature bath regulated at 25° ± 0.1° C, with 250 cc of 0.1 N hydrochloric acid used as the solvent.

The release rate of chloramphenicol thus obtained was 50% after 10 minutes and 85% after 60 minutes.

Separately, beta-1,4 glucan and chloramphenicol were pulverized independently, and 90 mg of beta-1,4 glucan and 10 mg of chloramphenicol were taken out and mixed. The same release test was carried out on the specimen this obtained, and resulted in the release rate of 20% and 40% after 10 minutes and 60 minutes respectively.

EXAMPLE 2

Following the method described in the Example 1, theophylline was added to beta-1,4 glucan at ratios of 5%, 10%, 100%, 150% and 1,000% and simultaneously pulverized. The amount of the specimen put into the pulverizer was 1 g in total. After pulverization, the specimen was subjected to a release test by use of 0.1 normal water solution of chloric acid as a releasing medium.

Determination of the dissolved volume was carried out using a U.V. spectrophotometer as to the filtrate through glass filter in a range of $\lambda = 270$ mu. Release rates were 72%, 70%, 71%, 68% and 65% after 10 minutes respectively, and 90%, 91%, 91%, 88% and 85% after 60 minutes respectively.

Separately, as a control group, beta-1,4-glucan and theophilline which had been prepared by pulverization prior to a release test were simply mixed so as to make the concentration of theophilline 5%, 10%, 100%, 500% and 1,000%, and subjected to the test by use of 0.1 normal water solution of chloric acid as a releasing medium following the preceding case. The result indicated only such release rates as 20% after 10 minutes and 64% after 60 minutes regardless of the concentration of theophilline.

As it is obvious in the present example, the simultaneous pulverization with beta-1,4-glucan resulted in sooner release of theophilline about 3.5 times after 10 minutes and about 1.5 times after 60 minutes as much as the control group respectively under almost every concentration of the ingredient, demonstrating marked efficiency.

EXAMPLE 3

Seventy-five parts of beta-1,4-glucan and 25 parts of therophilline were simultaneously pulverized in a large-size ball mill (capacity 7l). The amount of the specimen placed into the mill was 300 g. The specimen was taken out twelve hours after when the X-ray diffraction diagram ceased to show a peak, and uniformly mixed with 100 g of DMV 80-mesh lactose, 25 g of corn starch and 5 g of magnesium-stearate all together added thereto and compressed by a rotary tableting machine (Model RTS-9, made by Kikusui Seisakusho, Kyoto), at compressing pressure of 500 kg/cm² with 20 r.p.m. of disc rotation.

Making use of a die with 8 mm$\phi$ standard concave, the tablet weight was set to 200mg.

The hardness of the tablets was 7.0 kg, disintegration time in water was 8 minutes, and the coefficient of variation of weight was 3%. They satisfied the standard of Japanese Pharmacopoeia.

By putting two kinds of tablets thus obtained into 0.1 normal water solution of chloric acid, and the method applied to Example 2 was taken again to determine the release rate resulting in the table below which disclosed that the tablets made of a component simultaneously pulverized with beta-1,4-glucan showed sooner release, which indicated that tablets of an rapid release can be manufactured therefrom.

Release Rate

| Time | Tablets containing simultaneously pulverized | Tablets containing simple mixture |
|---|---|---|
| after 5 min. | 50% | 10% |
| 10 min. | 65% | 15% |
| 60 min. | 90% | 60% |

EXAMPLE 4

Mephenesin, a muscular relaxant, has a low melting point in a range somewhere near 70° C. Generally speaking, ingredients, when they are crushed by mechanical force, are accompanied by heat or chemical reaction by compression force, shearing force or abrasion force caused from such a mechanical action, requiring special care, particularly in case of a lower melting point substance.

One gram of mephenesin was put into the same shaker mill as used in the Example 1 and subjected to pulverization for 6 hours, where it was observed that mephenesin adhered onto the exterior surface of the ball and interior wall of the mill which might be effected by heat caused by compression force of the ball's impact.

On the other hand, the component of simultaneously pulverized 1 g of mephenesin with 10 g of beta-1,4-glucan brought about a satisfactory result owing to pulverization, where no adhesion was observed.

EXAMPLE 5

Three hundred grams of simultaneously pulverized beta-1,4-glucan and theophilline which had been obtained in the Example 3 were mixed with 100 g of ordinary lactose and 25 g of corn starch, to which 400 g of 3% starch mucilage was added as a binder. After kneading them all together in a planetary mixer made by Shinagawa Kogyosho, Tokyo granulation was performed by use of a speed mill made by Fuji Powder K. K., Tokyo through a screen of 5 mm perforation. Wet granules obtained therefrom were exposed under 40° C in a hot-air dryer for 12 hours. Dried granules were filtrated through a 16-mesh sieve to eliminate 60 mesh screenings, and magnesium stearate, 0.5% in weight to $-16 \sim +60$ mesh-screened matters, was added and mixed therewith to compress into tablets by a tableting machine, following the process applied in the Example 3.

The hardness of the tablets thus obtained was 10 kg and its disintegration time was 20 minutes. The coefficient of variation of weight was 2.5%. They satisfied the Japanese Pharmacopoeia.

On the other hand, beta-1,4-glucan and theophilline were pulverized independently, and 300 g of mixture thereof was prepared so that the concentration of theophilline was made to 25%, and subjected to wet granulation by adding lactose and corn starch exactly in the same manner as applied in the above example and then compressed into tablets by adding magnesium stearate.

The properties of the tablets obtained therefrom were such as 10 kg of hardness, 21 minutes of disintegration time and 2.4% of coefficient of variation of the weight.

Two kinds of the specimens obtained in the process above were subjected to a release test, which resulted in that the product which was simultaneously pulverized with beta-1,4-glucan demonstrated such sooner release as 3 times after 10 minutes, and 1.5 times after 60 minutes as the control group, proving that it is possible to manufacture drugs having a rapid release.

It is also predictable from the result above that the granules obtained from wet granulation can be used as they are, for manufacturing drugs having a rapid release.

Having thus described the invention what is claimed is:

1. The method of increasing the rate of solubility of a material of low solubility comprising mixing the material with beta-1, 4 glucan, and pulverizing the mixture.
2. The method of claim 1 wherein the material is a pharmaceutical.
3. The method of claim 1 wherein pulverization is carried to the extent that diffraction crystalline peaks cease to exist in an X-ray diffraction diagram.
4. The method of claim 2 including the additional step of incorporating the pulverized mixture into a solid pharmaceutical dosage form.
5. The method of claim 2 including the additional step of compacting the pulverized mixture into a tablet.